(12) United States Patent
Deno

(10) Patent No.: US 9,220,435 B2
(45) Date of Patent: Dec. 29, 2015

(54) SYSTEM AND METHOD FOR GENERATING ELECTROPHYSIOLOGY MAPS

(71) Applicant: St. Jude Medical, Cardiology Division, Inc., St. Paul, MN (US)

(72) Inventor: Don Curtis Deno, Andover, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 14/504,174

(22) Filed: Oct. 1, 2014

(65) Prior Publication Data

US 2015/0099992 A1 Apr. 9, 2015

Related U.S. Application Data

(60) Provisional application No. 61/888,719, filed on Oct. 9, 2013.

(51) Int. Cl.

| | | |
|---|---|---|
| *A61B 5/04* | (2006.01) | |
| *A61B 5/0468* | (2006.01) | |
| *G06F 19/00* | (2011.01) | |
| *A61B 5/00* | (2006.01) | |
| *A61B 5/042* | (2006.01) | |
| *A61B 5/0464* | (2006.01) | |
| *A61B 18/14* | (2006.01) | |
| *A61B 18/00* | (2006.01) | |

(52) U.S. Cl.
CPC ............... *A61B 5/0468* (2013.01); *A61B 5/042* (2013.01); *A61B 5/0464* (2013.01); *A61B 5/743* (2013.01); *A61B 18/1492* (2013.01); *G06F 19/3437* (2013.01); *A61B 5/0422* (2013.01); *A61B 2018/00577* (2013.01)

(58) Field of Classification Search
None
See application file for complete search history.

(56) References Cited

U.S. PATENT DOCUMENTS

| | | |
|---|---|---|
| 5,697,377 A | 12/1997 | Wittkampf |
| 5,983,126 A | 11/1999 | Wittkampf |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2008/0009758 A1 | 1/2008 | Voth |
| 2010/0274123 A1 | 10/2010 | Voth |
| 2012/0184858 A1 | 7/2012 | Harlev et al. |
| 2013/0245473 A1 | 9/2013 | Ramanathan et al. |

OTHER PUBLICATIONS

International Search Report and Written Opinion for PCT/US2014/058970 dated Jan. 14, 2015.
International Search Report and Written Opinion for PCT/US2014/058968 dated Jan. 23, 2015.
Gonzalez-Torrecilla et al., Non-Fluoroscopic Electroanatomical Mapping (CARTO System) in the Ablation of Atrial Tachycardias, Revista Espanola De Cardiologia, 2004, 57(1); 37-44.
Raymond W. Sy et al., Modern Electrophysiology Mapping Techniques, Heart, Lung and Circulation, 2012, 21:364-375, Elsevier Inc.

*Primary Examiner* — Brian T Gedeon
*Assistant Examiner* — Ankit Tejani
(74) *Attorney, Agent, or Firm* — Wiley Rein LLP

(57) ABSTRACT

A method of mapping cardiac electrical activity includes the acquisition of electrophysiological signals and using signal processing hardware to process such signals to identify lateness attributes thereof. If the lateness attribute exceeds a lateness threshold, then the corresponding point on the patient's heart can be designated as a therapy (e.g., ablation) target. It is also contemplated to use an upper bound on the lateness threshold, such that the corresponding point on the patient's heart is only designated as a therapy target if the lateness attribute both exceeds the lateness threshold and does not exceed the lateness bound. Both late activation ("Late-A") and late potential ("Late-P") attributes are contemplated.

17 Claims, 5 Drawing Sheets

SYSTEM AND METHOD FOR GENERATING ELECTROPHYSIOLOGY MAPS

CROSS-REFERENCE TO RELATED APPLICATIONS

This application claims the benefit of U.S. provisional application No. 61/888,719, filed 9 Oct. 2013, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for generating an electrophysiology map from data collected by an electrophysiology probe (e.g., a contact or non-contact mapping catheter).

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

BRIEF SUMMARY

Disclosed herein is a method of mapping cardiac electrical activity, including: acquiring an electrical signal indicative of electrical activity at a location on a patient's heart; inputting the electrical signal to a signal processor (e.g., signal processing firmware, hardware, and/or software); and using the signal processor to identify a lateness attribute of the electrical signal, compare the lateness attribute to a lateness threshold, and designate the location on the patient's heart as a therapy target when the lateness attribute of the electrical signal exceeds a lateness threshold. The lateness attribute can be a late activation ("Late-A") attribute or a late potential ("Late-P") attribute; in certain aspects, both a Late-A attribute and a Late-P attribute can be utilized.

When a Late-A attribute is used, the lateness threshold can be between 20 and 30 ms. Similarly, the lateness threshold for a Late-P attribute can be between 50 and 70 ms.

The electrical signal can be an electrogram ("EGM") signal or a surface electrocardiogram ("ECG" or "EKG") signal. It can also be representative of the electrical activity occurring on the epicardial or endocardial surface, or at other locations on or near the heart.

A plurality of electrical signals from a plurality of locations on the patient's heart can be acquired and processed by the signal processor. This repetition allows for multiple locations on the patient's heart to be designated as therapy targets. It also results in a data set that can be used to create and output a graphical representation of the electrical activity occurring on the patient's heart, such as a lateness map. It is contemplated that this graphical representation (e.g., a Late-A map) can be marked with visual indicators of the locations on the patient's heart that have been designated as therapy targets.

In embodiments, an upper bound on the lateness attribute (a "lateness bound") is also defined. In these aspects, the lateness attribute for the location on the patient's heart is compared to the lateness bound, and designated as a therapy target when the lateness attribute of the electrical signal both exceeds the lateness threshold and does not exceed the lateness bound. Suitable lateness bounds are between 80 ms and 200 ms. For example, 100 ms is a suitable lateness bound for Late-A mapping.

Both the lateness threshold and the lateness bound can be defined based on user input. They may also be adjusted "on the fly," which can alter both past and future points that are designated as therapy targets.

Also disclosed herein is a method of mapping cardiac electrical activity, including: acquiring an electrical signal indicative of electrical activity at a point on a patient's heart; inputting the electrical signal to a signal processor; and using the signal processor to identify a lateness attribute of the electrical signal and designate the point on the patient's heart as a therapy target when the lateness attribute of the electrical signal falls within a lateness band. The lateness band, in turn, can be defined by a user-defined lateness threshold (e.g., between 20 and 30 ms) at its lower end and by a user-defined lateness bound (e.g., no greater than 100 ms) at its upper end.

In another aspect, a system for mapping cardiac electrical activity includes: a lateness analysis processor configured to receive, as input, an electrical signal indicative of electrical activity at a location on a patient's heart; to analyze the electrical signal to identify a lateness attribute of the electrical signal; to compare the lateness attribute to a lateness threshold; and to designate the location on the patient's heart as a therapy target when the lateness attribute of the electrical signal exceeds a lateness threshold. The lateness analysis processor can further be configured to designate the location on the patient's heart as a therapy target when the lateness attribute of the electrical signal both exceeds a lateness threshold and does not exceed a lateness bound.

The system can also include a mapping processor configured to: generate and output a graphical representation of electrical activity on a portion of the patient's heart from a plurality of electrical signals indicative of electrical activity at a plurality of locations on the patient's heart, the plurality of locations on the patient's heart including a plurality of points designated as therapy targets; and mark the graphical representation with visual indicators of the plurality of locations on the patient's heart designated as therapy targets.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses and systems for the creation of electrophysiology maps (e.g., electrocardiographic maps). For purposes of illustration, several exemplary embodiments will be described in detail herein in the context of a cardiac electrophysiology procedure. It is contemplated, however, that the methods, apparatuses, and systems described herein can be utilized in other contexts.

Figure 1:
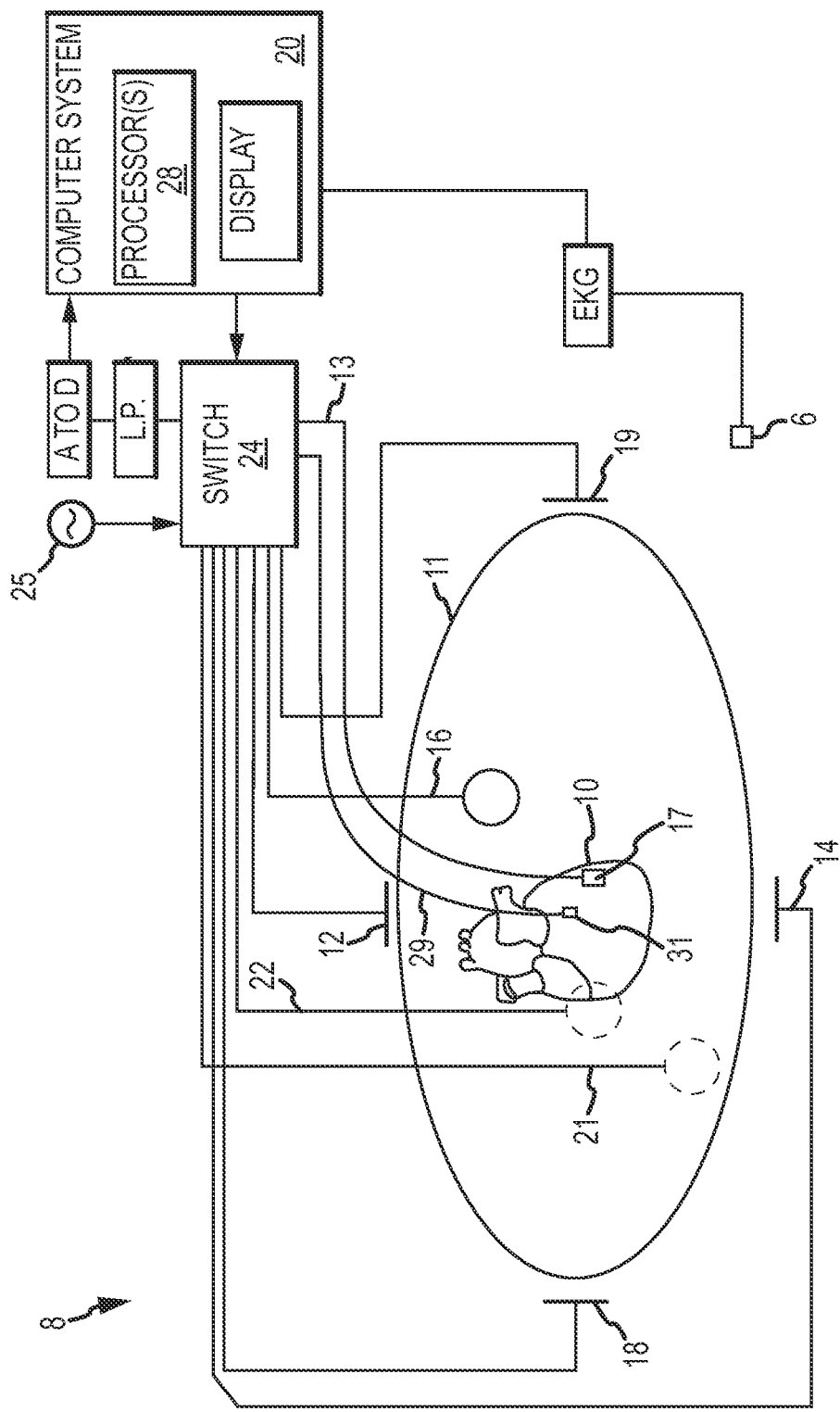
FIG. 1 is a schematic diagram of an electrophysiology system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion. This representative catheter electrode 17 can be referred to as a "measurement electrode." Typically, multiple electrodes on catheter 13, or on multiple such catheters, will be used. In one embodiment, for example, system 8 may utilize sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
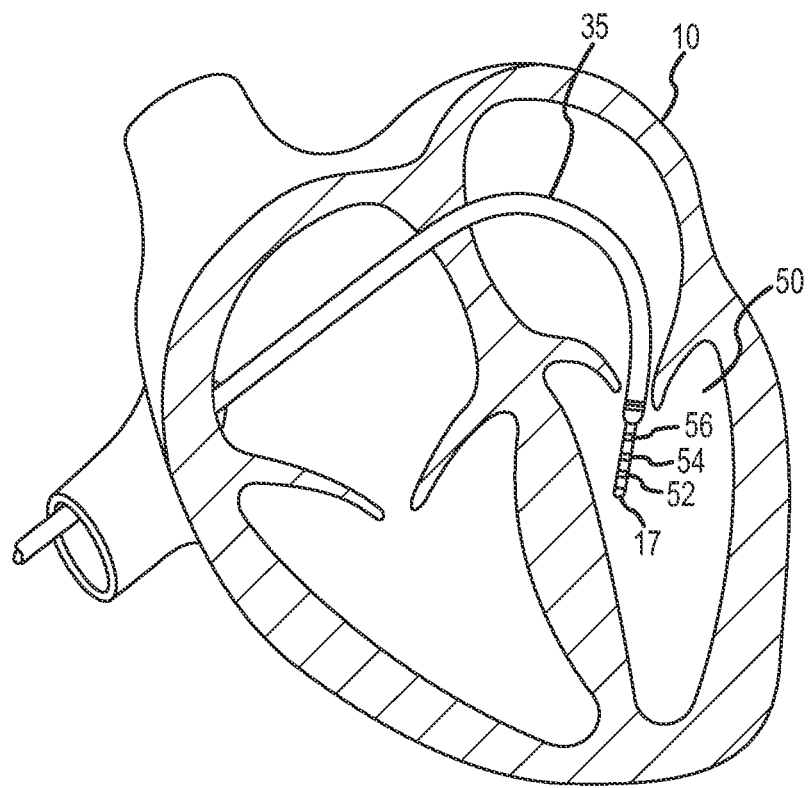
FIG. 2 depicts an exemplary catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990, 370; 6,978,168; 6,947,785; 6,939,309; 6,728,562; 6,640,119; 5,983,126; and 5,697,377.

In an electrophysiology study associated with the treatment of cardiac arrhythmias, such as ventricular tachycardia ("VT"), it may be useful to identify a lateness attribute of the electrophysiological signal. Indeed, lateness attributes can even be identified when the patient is in sinus rhythm. Lateness attributes, which include both late potential ("Late-P") and late activation ("Late-A") attributes, both of which are discussed further below, suggest that some myocardial fibers are functional near the measurement electrode, but that they are few in number and therefore low in amplitude and conducting slowly. These conditions are understood to be ripe for the initiation and sustainment of VT; such tissue also lacks substantial mechanical pump function. Thus, these points are desirable targets for ablation to treat VT. It is therefore contemplated that points on a patient's heart where the lateness attribute exceeds a lateness threshold, but does not exceed a lateness bound, will be designated as therapy targets.

Figure 3:
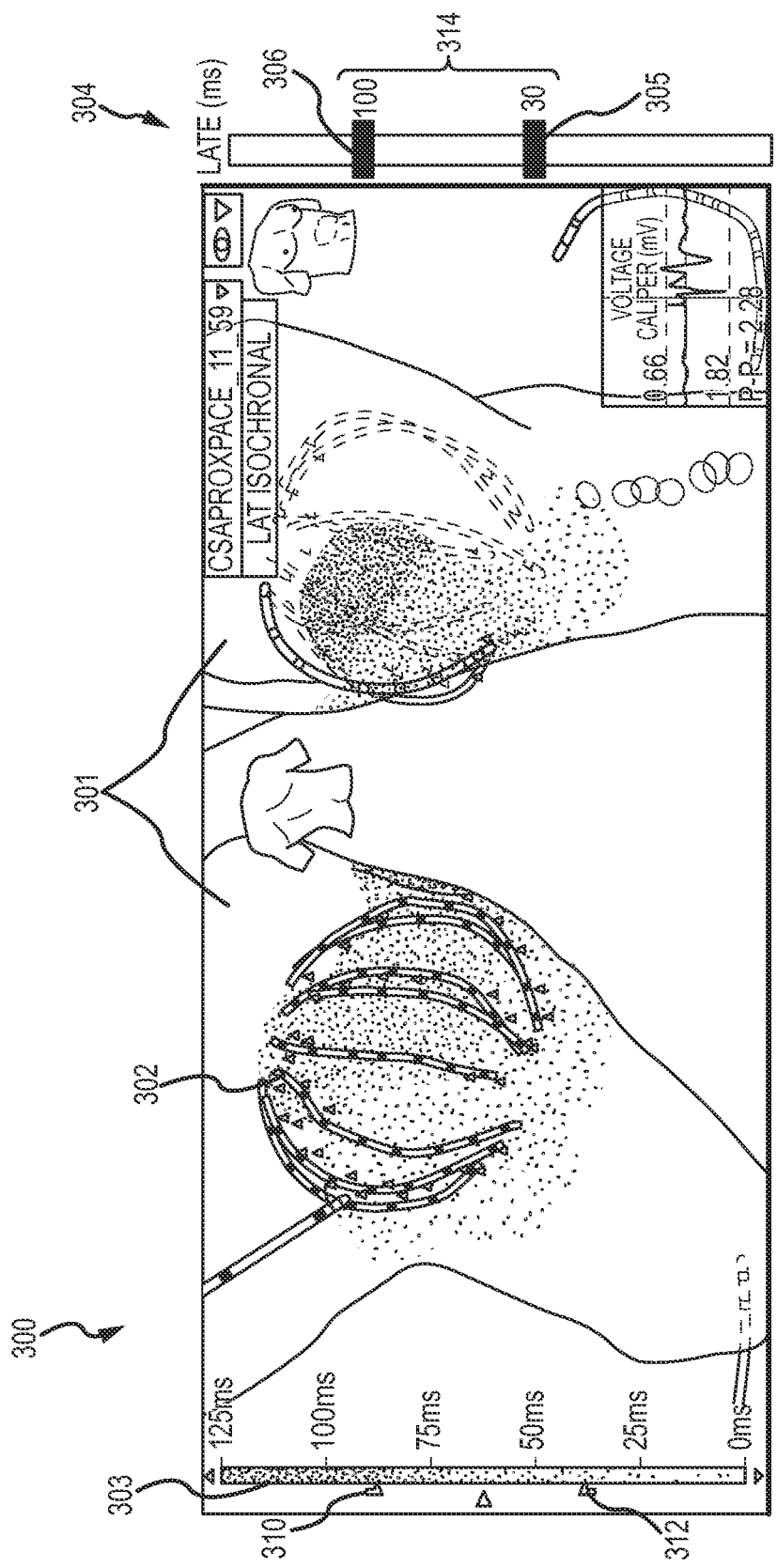
FIG. 3 is a representative lateness map according to the teachings herein.

A lateness map, as disclosed herein, is an electrophysiology map that depicts the lateness attributes of the electrical activity at various points on a cardiac surface. FIG. 3 depicts an exemplary lateness map 300 generated using various aspects disclosed herein and data collected and processed using system 8 (e.g., using computer system 20).

In general, electrophysiology maps, such as lateness map 300, are created from a plurality of electrophysiology data points, each of which includes both measured electrophysiology data (e.g., cardiac electrograms ("EGMs")) and location data (e.g., information regarding the location of catheter 13 and/or the electrodes thereon), allowing the measured electrophysiology information to be associated with a particular location in space (that is, allowing the measured electrophysiology information to be interpreted as indicative of electrical activity at a point on the patient's heart).

Lateness map 300 includes a graphical representation 301 of the portion of the patient's heart that is being mapped, and also depicts a graphical representation 302 of the mapping catheter itself.

An index 303 shows the color- or grey-scale (or other presentation, such as stippling) with which the graphical representation 301 of the heart is generated (e.g., what color or shade of grey corresponds to a particular lateness attribute). Index 303 includes upper bound indicator 310 and lower bound indicator 312. All points with lateness values above upper bound indicator 310 can be presumed to be equally desirable ablation targets. Thus, the presentation scale above upper bound indicator 310 can be undifferentiated (that is, all points with lateness values in excess of upper bound indicator 310 can be presented in the same color, the same level of greyscale, or the like.

Likewise, all points with lateness values below lower bound indicator 312 can be presumed to be equally undesirable ablation targets. Thus, the presentation scale below lower bound indicator 312 can also be undifferentiated.

Between upper and lower bound indicators 310, 312, however, variations in presentation can be used to aid a practitioner in identifying desirable ablation targets.

Also shown in FIG. 3 is a slider bar 304 that can be used to define the lateness threshold and lateness bound, as described in detail below.

The ordinarily skilled artisan will be familiar with various modalities for the acquisition and processing of electrophysiology data points (including, for example, both contact and non-contact electrophysiological mapping), such that further discussion thereof is not necessary to the understanding of the lateness mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the lateness maps disclosed herein.

Figure 4:
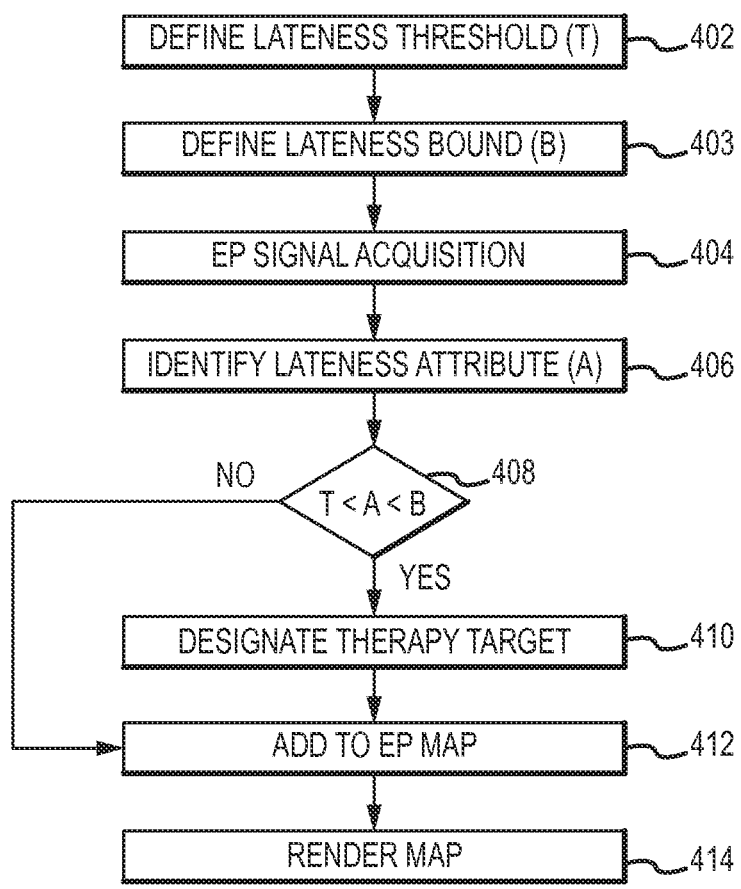
FIG. 4 is a flowchart of representative steps that can be followed to create a lateness map.

FIG. 4 is a flowchart of representative steps that can be carried out to create a lateness map, including the identification of therapy targets. In some embodiments, for example, the flowchart may represent several exemplary steps that can be carried out by the computer 20 of FIG. 1 (e.g., by one or more processors 28) to generate a lateness map such as that described herein with respect to FIG. 3. It should be understood that the representative steps described below can be either hardware- or software-implemented. For the sake of explanation, the term "signal processor" is used herein to describe both hardware- and software-based implementations of the teachings herein.

In block 402, a lateness threshold T is defined. Suitable values for lateness thresholds will be discussed in greater detail below. It should be understood that the lateness threshold need not be system defined, but can be user selectable and adjustable, for example using a slider bar 305 as shown schematically in FIG. 3. Below the lateness threshold T (e.g., above 30 ms in FIG. 3), one can presume that the "lateness" is part of the original QRS wave rather than a separate "late" feature.

In block 403, a lateness bound B is defined. Suitable values for lateness bounds will be discussed in greater detail below. It should be understood that the lateness bound need not be system defined, but can be user selectable and adjustable, for example using a slider bar 306 as shown schematically in FIG. 3. Above the lateness bound B (e.g., above 100 ms in FIG. 3), one can presume that the "lateness" is so far removed from the original QRS wave that it is likely an artifact rather than a separate "late" feature.

Together, the lateness threshold T and lateness bound B define a lateness band 314. Points that are suitable targets for ablation and/or other therapies are likely to have lateness attributes falling within this band. The ordinarily skilled artisan will recognize, from the description herein, suitable bands for both Late-P and Late-A attribute lateness maps.

In block 404, an electrical signal indicative of electrical activity at a point on the patient's heart, such as an ECG or an EGM, is acquired. In many electrophysiology studies, signal acquisition is done in real time (e.g., via collection using ECG leads or electrodes 17, 52, 54, and 56 on catheter 13), but the teachings herein can also be applied to previously collected electrophysiology data. The electrical signal will also be associated with location data.

In block 406, the acquired signal is processed to identify a lateness attribute A. As noted above, useful lateness attributes include both Late-P and Late-A attributes. A Late-P attribute is measured from a common reference point, such as from the peak of a surface ECG R wave, to the end of activity at the site being mapped.

A Late-A attribute, on the other hand, is measured from the last large deflection (indicating the end of major local depolarization) to the end of low amplitude activity at that site (indicating the end of nearby depolarizations of small myocardial fibers or pathways, such as might occur in a critical arrhythmia pathway). This is advantageous, as it allows a Late-A attribute to be identified for any electrophysiological signal, whether EGM or ECG, without reference to any overall trigger (e.g., a $V_{PACE}$ event and/or a specific part of a surface QRS or endocardial EGM deflection).

Figure 5:
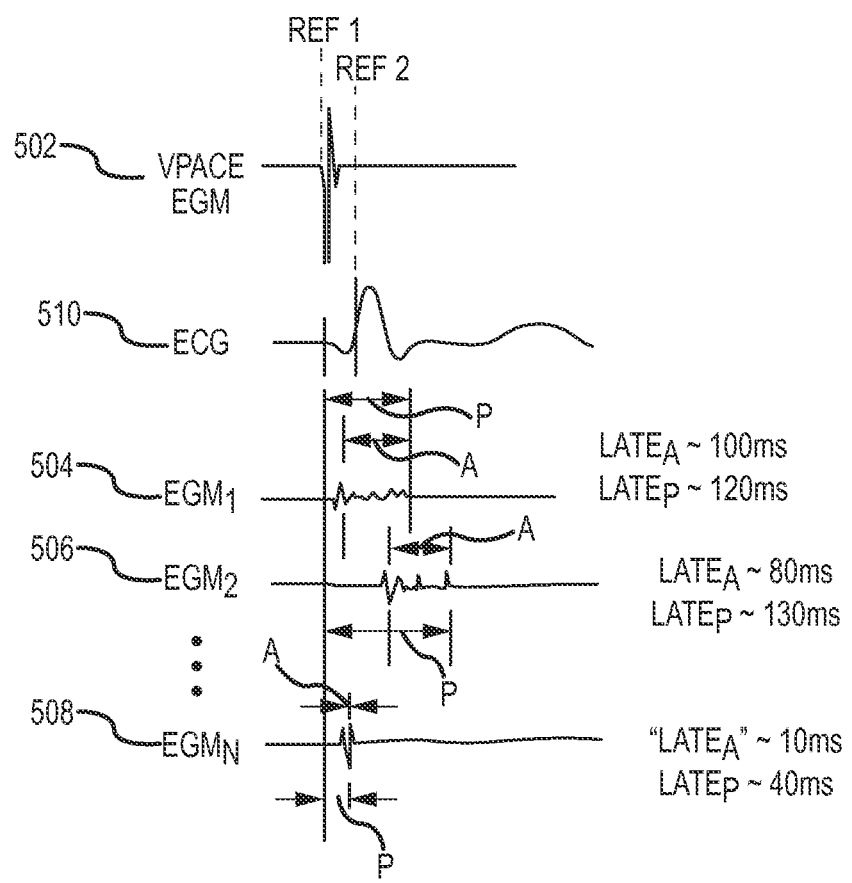
FIG. 5 illustrates several exemplary electrophysiological signals, annotated with their respective lateness attributes.

To aid in the understanding of the instant disclosure, FIG. 5 depicts several illustrative electrophysiology signals, including four representative EGMs ($V_{PACE}$ 502, $EGM_1$ 504, $EGM_2$ 506, and $EGM_N$ 508), and one representative ECG signal 510. $EGM_1$, $EGM_2$, and $EGM_N$ are annotated to illustrate their Late-A and Late-P attributes. As shown in FIG. 5, the Late-P attributes of the various signals are measured from the point "REF 1" as annotated in $V_{PACE}$ EGM 502.

The lateness attribute is compared to the lateness threshold T and lateness bound B in decision block 408. If the lateness attribute exceeds the lateness threshold T, but remains below the lateness bound B, then the corresponding cardiac surface point is designated a therapy target in block 410.

With respect to Late-A attributes, the points most likely to be desirable ablation targets are those that, when using band pass filtering of 50-500 Hz on bipoles, persist for up to 100 ms following the majority of local depolarization. That is, the most suitable ablation or therapy targets are those where the Late-A attribute is up to 100 ms. Thus, for example, the lateness threshold T for a Late-A attribute can be set between 20 and 30 ms (recall that points with a lateness attribute in excess of the lateness threshold can be designated as a therapy (e.g., ablation) target). Likewise, the lateness bound B for a Late-A attribute can be set at 100 ms. The use of a lateness bound minimizes errors where subsequent beats are misinterpreted as late activity. Referring to the representative EGMs in FIG. 5, the surface locations corresponding to $EGM_1$ 504, with a Late-A attribute of about 100 ms, and $EGM_2$ 506, with a Late-A attribute of about 80 ms, would be designated as therapy targets.

For Late-P attributes, on the other hand, the lateness threshold T can be set between 50 and 70 ms, and the lateness bound B can be set between 80 ms and 200 ms. Referring to the representative EGMs in FIG. 5, therefore, the surface locations corresponding to $EGM_1$ 504, with a Late-P attribute of about 120 ms, and $EGM_2$ 506, with a Late-P attribute of about 130 ms, would once again be designated as therapy targets (provided that the lateness bound B is set to at least 130 ms).

In block 412, an electrophysiology data point is added to the electrophysiology map. In some aspects, only designated therapy targets are added to the electrophysiology map. In other aspects, all electrophysiology data points are added to the electrophysiology map, so as to allow for the creation of a graphical rendering of lateness attributes over a continuous area, rather than only at those discrete points where the lateness attribute exceeds the lateness threshold.

Steps 404, 406, 408, 410, and 412 will generally be repeated numerous times and for numerous points on the cardiac surface during the course of an electrophysiology study, thereby yielding a plurality of electrophysiology data points (and likely a plurality of designated therapy targets). Once sufficient electrophysiological data has been collected, a lateness map can be rendered in block 414 (see, e.g., FIG. 3) from the collected plurality of electrophysiology data points.

As the ordinarily skilled artisan will appreciate from this disclosure, the lateness map of block 414 can be rendered in a traditional manner (e.g., with different colors or grayscales corresponding to different values or ranges of values for the depicted lateness attribute(s)). In addition, the lateness map can be enhanced with icons or other visual cues to graphically reflect those cardiac surface points that were designated as therapy targets based on their lateness attributes.

Although several embodiments of this invention have been described above with a certain degree of particularity, those skilled in the art could make numerous alterations to the disclosed embodiments without departing from the spirit or scope of this invention.

For example, both Late-A and Late-P attributes can be used in conjunction to identify therapy targets (e.g., sites for ablation).

As another example, although the description above pertains to endocardial maps (that is, maps of the electrophysiological activity occurring on the interior surface of the heart), the teachings herein can also be applied to epicardial maps (e.g., maps of the electrophysiological activity occurring on the exterior surface of the heart).

The teachings herein can also be applied to atrial mapping, such as mapping accessory pathways that can be responsible for supraventricular tachycardias.

Further, the therapy need not be ablation. For example, lateness attributes, indicative of transitions to a fibrous valve annulus or other anatomic feature, may be useful to identify the insertion or anchor site for a transcatheter valve or occlusion device. Similarly, lateness attributes may be useful in the delivery of stem cell and/or gene therapies.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac electrical activity, comprising:
   acquiring an electrical signal indicative of electrical activity at a location on a patient's heart;
   inputting the electrical signal to a signal processor; and
   using the signal processor:
      identifying at least one lateness attribute of the electrical signal, the at least one lateness attribute comprising at least one of a late activation ("Late-A") attribute and a late potential ("Late-P") attribute;
      comparing the at least one lateness attribute to at least one lateness threshold; and
      designating the location on the patient's heart as a therapy target when the at least one lateness attribute of the electrical signal exceeds the at least one one lateness threshold.

2. The method according to claim 1, wherein the at least one lateness threshold comprises a Late-A threshold between 20 and 30 ms.

3. The method according to claim 1, wherein the at least one lateness threshold comprises a Late-P threshold between 50 and 70 ms.

4. The method according to claim 1, wherein the electrical signal comprises an electrogram ("EGM") signal.

5. The method according to claim 1, wherein the electrical signal comprises an electrocardiogram ("ECG" or "EKG") signal.

6. The method according to claim 1, further comprising repeating the acquiring, inputting, identifying, and designating steps for a plurality of locations on the patient's heart, thereby designating a plurality of locations on the patient's heart as therapy targets.

7. The method according to claim 6, further comprising, using the signal processor:
   outputting a graphical representation of electrical activity on a portion of the patient's heart; and
   marking the graphical representation with visual indicators of the locations on the patient's heart designated as therapy targets.

8. The method according to claim 7, wherein the graphical representation of electrical activity on a portion of the patient's heart comprises a lateness map.

9. The method according to claim 8, wherein the lateness map comprises a Late-A map.

10. The method according to claim 1, further comprising comparing the at least one lateness attribute to at least one lateness bound, and wherein the location on the patient's heart is designated as a therapy target when the at least one lateness attribute of the electrical signal exceeds the at least one lateness threshold and the at least one lateness attribute of the electrical signal does not exceed the at least one lateness bound.

11. The method according to claim 10, wherein the at least one lateness bound comprises a Late-A bound between 80 ms and 180 ms.

12. A method of mapping cardiac electrical activity, comprising:
   acquiring an electrical signal indicative of electrical activity at a point on a patient's heart;
   inputting the electrical signal to a signal processor; and
   using the signal processor:
      identifying a lateness attribute of the electrical signal; and
      designating the point on the patient's heart as a therapy target when the lateness attribute of the electrical signal falls within a lateness band defined between two times.

13. The method according to claim 12, wherein the lateness band is defined by a user-defined lateness threshold at its lower end and by a user-defined lateness bound at its upper end.

14. The method according to claim 13, wherein the lateness threshold is between 20 ms and 30 ms and the lateness bound is no greater than 100 ms.

15. A system for mapping cardiac electrical activity, comprising:
   a lateness analysis processor configured to:
      receive, as input, an electrical signal indicative of electrical activity at a location on a patient's heart;
      analyze the electrical signal to identify a lateness attribute of the electrical signal, wherein the lateness attribute of the electrical signal comprises a time period; and
      designate the location on the patient's heart as a therapy target when the lateness attribute of the electrical signal exceeds a lateness threshold, wherein the lateness threshold comprises a time period.

16. The system according to claim 15, wherein the lateness analysis processor is further configured to designate the location on the patient's heart as a therapy target when the lateness attribute of the electrical signal both exceeds a lateness threshold and does not exceed a lateness bound.

17. The system according to claim 15, further comprising a mapping processor configured to:
   generate and output a graphical representation of electrical activity on a portion of the patient's heart from a plurality of electrical signals indicative of electrical activity at a plurality of locations on the patient's heart, the plurality of points on the patient's heart including a plurality of locations designated as therapy targets; and
   mark the graphical representation with visual indicators of the plurality of locations on the patient's heart designated as therapy targets.

* * * * *

UNITED STATES PATENT AND TRADEMARK OFFICE
CERTIFICATE OF CORRECTION

| | | |
|---|---|---|
| PATENT NO. | : 9,220,435 B2 | Page 1 of 1 |
| APPLICATION NO. | : 14/504174 | |
| DATED | : December 29, 2015 | |
| INVENTOR(S) | : Don Curtis Deno | |

It is certified that error appears in the above-identified patent and that said Letters Patent is hereby corrected as shown below:

In the Claims:

Column 9, claim 1, line 63, kindly delete "one one" and replace with --one--.

Signed and Sealed this
Nineteenth Day of April, 2016

Michelle K. Lee
*Director of the United States Patent and Trademark Office*